United States Patent
Bohanan et al.

(10) Patent No.: US 6,997,872 B1
(45) Date of Patent: Feb. 14, 2006

(54) VARIABLE FORCE SURGICAL RETRACTOR ASSEMBLY

(75) Inventors: Bryan S. Bohanan, Loveland, OH (US); Kenneth F. Kovach, Cleveland, OH (US); Daniel S. Furst, Concord Township, OH (US)

(73) Assignee: Biomec, Inc., Cleveland, OH (US)

( * ) Notice: Subject to any disclaimer, the term of this patent is extended or adjusted under 35 U.S.C. 154(b) by 7 days.

(21) Appl. No.: 10/294,309

(22) Filed: Nov. 14, 2002

Related U.S. Application Data

(60) Provisional application No. 60/332,748, filed on Nov. 14, 2004.

(51) Int. Cl.
*A61B 1/32* (2006.01)

(52) U.S. Cl. .................................................... 600/210

(58) Field of Classification Search ................ 600/206, 600/210, 217, 219, 226, 227, 215, 229, 234
See application file for complete search history.

(56) References Cited

U.S. PATENT DOCUMENTS

| | | | |
|---|---|---|---|
| 1,401,190 A * | 12/1921 | Risley ......................... | 600/215 |
| 4,467,791 A | 8/1984 | Cabrera et al. | |
| 5,184,604 A * | 2/1993 | Brillante ...................... | 600/206 |
| 5,351,679 A | 10/1994 | Mayzels et al. | |
| 5,477,948 A | 12/1995 | Stevens | |
| 5,628,343 A | 5/1997 | Lan | |
| 5,830,231 A * | 11/1998 | Geiges, Jr. ................... | 606/205 |
| 5,921,918 A | 7/1999 | Riza | |
| 6,063,025 A | 5/2000 | Bridges et al. | |
| 6,102,439 A * | 8/2000 | Smithson et al. ........... | 280/805 |
| 6,296,609 B1 * | 10/2001 | Brau .......................... | 600/210 |

\* cited by examiner

*Primary Examiner*—Pedro Philogene
(74) *Attorney, Agent, or Firm*—Pearne & Gordon LLP

(57) ABSTRACT

A surgical retractor assembly for providing a generally constant retracting force at a fixation site on a patient despite possible movements of the fixation site during application of the retracting force. The retractor assembly comprises a support structure engaging element for providing communication between the surgical retractor assembly and a support structure; a retractor guide for receiving a first end of a retracting member, the retractor guide being coupled to the support structure engaging element, wherein the retractor guide is displaceable relative to the support structure engaging element; and a biasing structure that provides the retracting force.

14 Claims, 5 Drawing Sheets

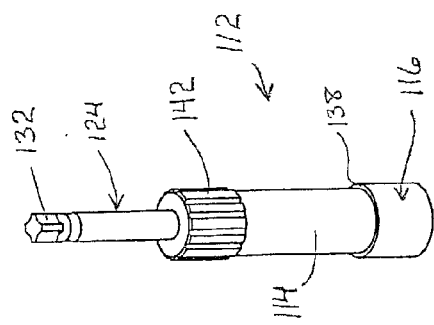
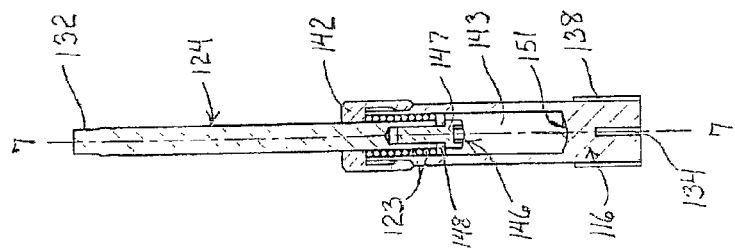
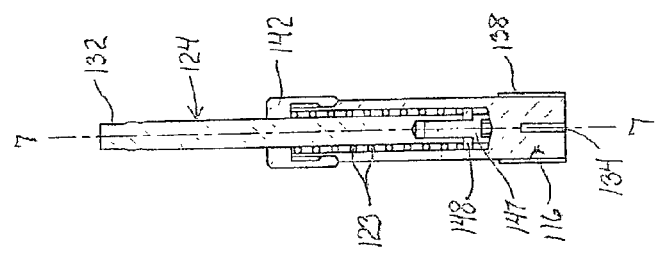
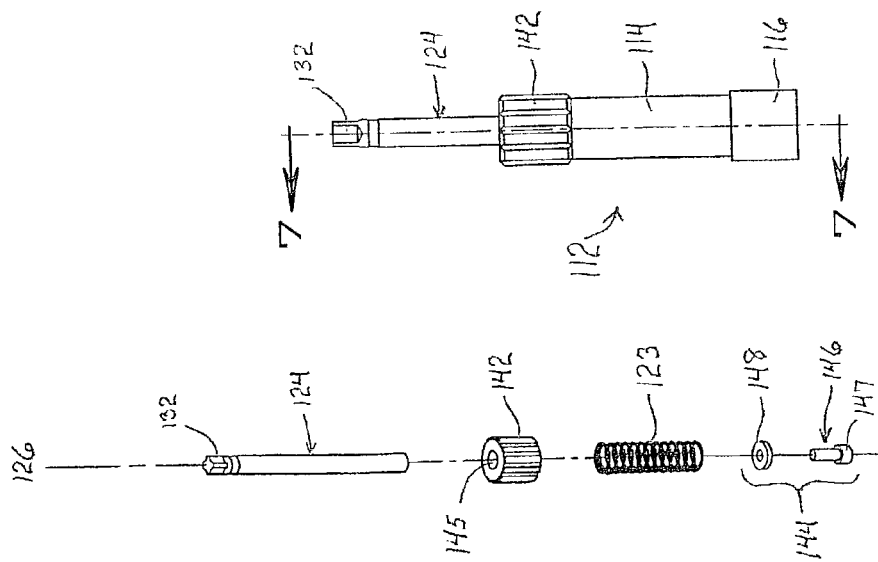
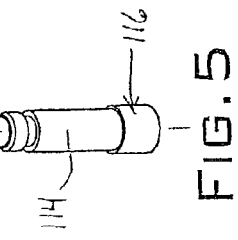

VARIABLE FORCE SURGICAL RETRACTOR ASSEMBLY

BACKGROUND OF THE INVENTION

1. Field of the Invention

The present invention relates generally to surgical instrument holders, and more particularly to a variable force surgical retractor assembly for providing a generally constant retracting force at a desired fixation site despite the possible movement of the fixation site.

2. Description of Related Art

Retractors are commonly used in surgical procedures to provide a surgeon with an unobstructed view of inner portions of a patient's body cavity during a surgical procedure. The retractors are positioned within the cavity of a patient at a fixation site where the retractors contact the object being retracted. The retractors relocate objects obstructing the surgeon's view such as tissue, organs, or other members of the patient. Typically, one or more surgical assistants insert a retractor, or retractors, into an incision surgically created in the patient and hold the retractor(s) in place while the surgeon performs the surgical procedure. The need for surgical assistants to hold the retractor(s) increases the cost of the surgical procedure, and the presence of the surgical assistants provides additional obstacles, such as hands and arms, that the surgeon must avoid during the surgical procedure. Further, The assistants are not able to hold the retractor(s) to maintain a generally constant retracting force on the object being retracted during a lengthy surgical procedure due to fatigue.

Retractor assemblies have been developed to supplant the use of surgical assistants and hold a retractor in place. Typically, the assembly engages an end of the retracting member to hold the retracting member in place relative to the item being retracted. For simplicity, the term "retracting member" is used generally to describe a member that mayor may not include other features, such as a handle, for example, used to apply a retracting force at a fixation site on an object obstructing the surgeon's view during a surgical procedure. Conventional retractor assemblies that accept such retracting members do so by rigidly holding the retracting members in one location. As the fixation site moves during the surgical procedure, such as when tissue being retracted is dissected, or when relaxation of the skin surrounding the tissue being retracted occurs and the skin's elastic properties begin to weaken, for instance, the retracting member being held by a conventional retracting member assembly does not move and loses contact with the fixation site. When this happens, the item that the retracting force was initially applied to often returns to the position it was in before being retracted, and once again obstructs the view of the surgeon performing the surgical procedure.

Retracting members that are capable of being repositioned to maintain the retracting force on an item sufficient to ensure the surgeon has free access to the patient's body cavity exist in the art. An example of such a repositionable apparatus is a retracting member assembly that includes retracting hooks fastened to an end of a ball-and-link chain. The hooks engage the tissue surrounding an incision while the chain is extended to a suitable length. To maintain the length of the chain and thereby maintain the retracting force on the tissue, the balls of the chain communicate with notches formed along the periphery of a platform to restrict further extension of the chain. When the tissue being retracted moves during the surgical procedure, the surgeon, or an assistant, must manually manipulate the length of the chain to allow communication between a ball, located further along the length of the chain closer to the hook, and the notch. This shortens the length of the extended chain and once again provides the retracting force on the tissue. Every time the tissue moves during the surgical procedure and further retraction of the tissue is desired, this process of manually manipulating the length of the chain must be repeated. This requires a momentary cessation of the surgical procedure to manually manipulate the length of the chain, and if performed many times, may prolong a surgical procedure. If repeated manipulation of the chain is not performed, though, the tissue will obstruct the surgeon's view of the interior of the patient's body cavity.

Alternate retracting member assemblies have been developed to permit adjustment of the retracting member to maintain the retracting force applied by the retracting member on objects that move during a surgical procedure. Typically, these assemblies include advanced pressure sensing and control circuitry that is expensive and bulky for an operating room where space for equipment is often limited.

Accordingly, there is a need in the art for a surgical retractor assembly for providing a generally constant retracting force at a fixation site on a patient despite the possible movement of the fixation site during application of the retracting force.

BRIEF SUMMARY OF THE PRESENT INVENTION

The present invention, according to one embodiment, is a surgical retractor assembly for providing a generally constant retracting force at a fixation site on a patient despite the possible movement of the fixation site during application of the retracting force, the retractor assembly comprising a support structure engaging element for providing communication between the surgical retractor assembly and a support structure; a retractor guide for receiving a first end of a retracting member, the retractor guide being coupled to the support structure engaging element, wherein the retractor guide is displaceable relative to the support structure engaging element; and a biasing structure that provides the retracting force. The retractor guide according to one embodiment of the present invention is slidably coupled to a body portion for permitting linear translation of the retractor guide relative to the body portion.

According to another embodiment of the present invention, a surgical retractor assembly comprises a support structure engaging element for providing communication between the surgical retractor assembly and a support structure; a retractor guide for receiving a first end of a retracting member, the retractor guide being coupled to the support structure engaging element, wherein the retractor guide is displaceable relative to the support structure engaging element; and a biasing structure that provides the retracting force. Unlike the embodiment above, the retractor guide according to this embodiment is fixed at an end of a body portion, and displacement of the retractor guide relative to the support structure engaging element is provided by telescopic adjustment of the support structure engaging element relative to the body portion.

BRIEF DESCRIPTION OF THE DRAWINGS

The foregoing and other features and advantages of the present invention will become apparent to those skilled in the art to which the present invention relates upon reading the following description with reference to the accompanying drawing, in which:

FIG. 5 is an exploded view of a surgical retractor assembly in accordance with the present invention;

FIG. 6 is a side view of the surgical retractor assembly in FIG. 5 assembled;

FIG. 7 is a cross sectional view of the surgical retractor assembly shown in FIG. 6 taken along line 7—7, the surgical retractor assembly being illustrated in an unextended position;

FIG. 8 is a cross sectional view of the surgical retractor assembly shown in FIG. 6 taken along line 7—7, the surgical retractor assembly being illustrated in an extended position;

FIG. 9 is a perspective view of a surgical retractor assembly in accordance with the present invention;

DETAILED DESCRIPTION OF EXAMPLE EMBODIMENTS

Figure 1:
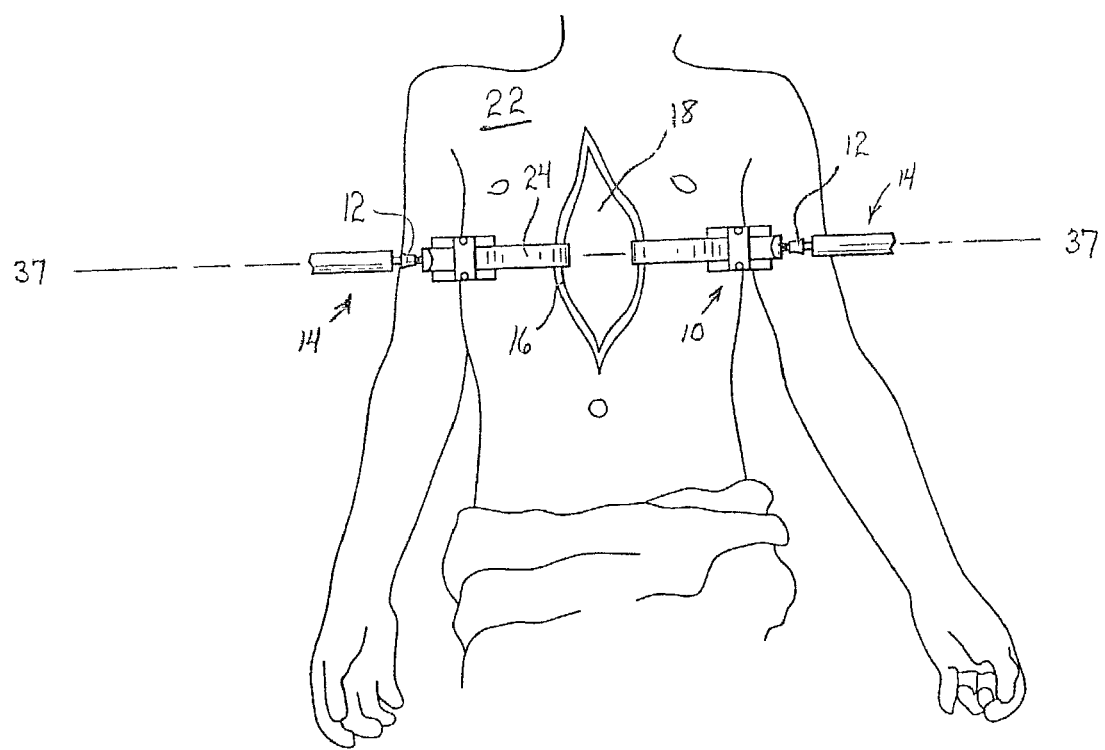
FIG. 1 is an illustrative view of a pair of surgical retractor assemblies in accordance with the present invention being used to retract tissue adjacent to an incision in a patient.

Certain terminology is used herein for convenience only and is not to be taken as a limitation on the present invention. Further, in the drawings, the same reference numerals are employed for designating the same elements throughout the fifteen figures, and in order to clearly and concisely illustrate the present invention, certain features may be shown in somewhat schematic form.

Referring to FIG. 1, an embodiment of a surgical retractor assembly 10 according to the present invention is illustrated in use during a surgical procedure. The retractor assembly 10 is operatively fastened to an accepting end 12 of a support structure 14 to retract tissue 16 adjacent an incision 18 in a patient 22. While the present invention is described in detail below providing a retracting force on tissue 16, the present invention is equally capable of providing a retracting force on any object where retraction is desired. During the surgical procedure, it is possible for the dimensions of the incision 18 to change due to the dissection of the tissue 16, or the relaxation of skin surrounding the tissue 16 after a prolonged period of retraction, for example. When movement of the tissue 16 occurs, a retracting member 24 transmitting a retracting force to the tissue 16 is displaced relative to a support structure engaging element 46 to maintain the retracting force on the tissue 16 with a magnitude similar to that applied to the tissue 16 prior to movement of the tissue 16.

Figure 2:
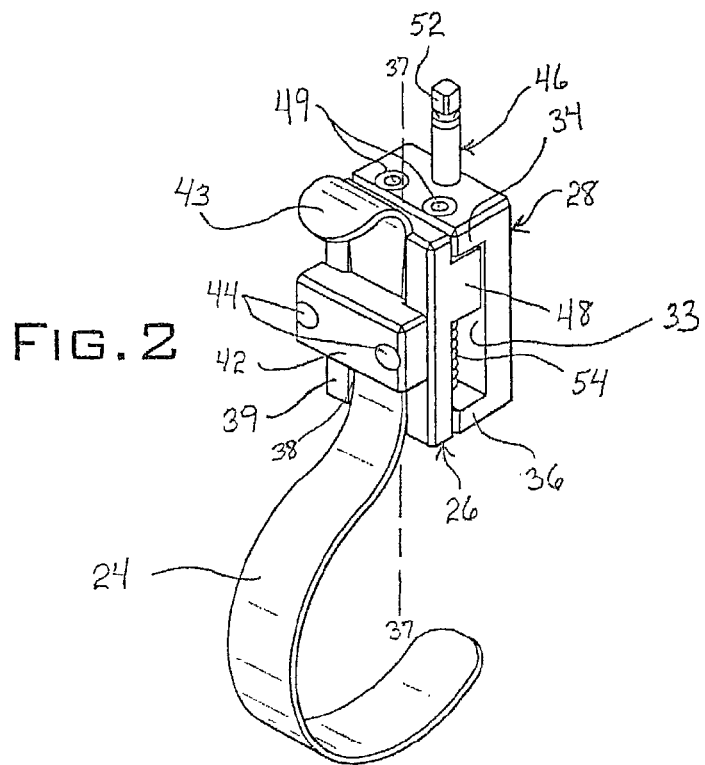
FIG. 2 is a perspective view of a surgical retractor assembly in accordance with the present invention, the surgical retractor assembly supporting a retracting member.

FIG. 2 is a perspective view of the retractor assembly 10 illustrated during use in FIG. 1. As shown, the retractor assembly 10 comprises a retractor guide 26 operatively coupled to the support structure engaging element 24 by a body portion 28 having a plurality of generally straight guides 32 disposed at a first side 33 of the body portion 28. The guides 32 extend between a first end block 34 and a second end block 36 to limit the motion of the retractor guide 26 to a generally linear displacement along an axis 37 over a length of the body portion 28 between the first end block 34 and the second end block 36.

Compatible features (not shown) of a communicating portion 48 of the retractor guide 26 communicate with the guides 32 to allow linear translation of the retractor guide 26 between the first and second end blocks 34, 36 along the axis 37. By way of example in FIGS. 2–4, the guides 32 are rods that extend between the first and second end blocks 34, 36. The rods in FIG. 2 are secured to the body portion 28 by fasteners 49, such as screws, pins, bolts, rivets, clips, or snaps, for example, or any other fastener capable of releasably securing the rods to the body portion 28, inserted through apertures in the first end block 34. Similarly, opposite ends of the rods are received by apertures in the second end block 36. The apertures in the second end block 36 either extend partially into the second end block 36 forming sockets (not shown) to receive the opposite ends of the rods, or, extend all the way through the second end block 36 allowing additional fasteners to pass therethrough to hold the opposite ends of the rods in place. The rods extend through holes or apertures (not shown), for example, formed in the communicating portion 48 of the retractor guide 26 as the compatible features to operatively couple the retractor guide 26 to the body portion 28.

Figure 3:
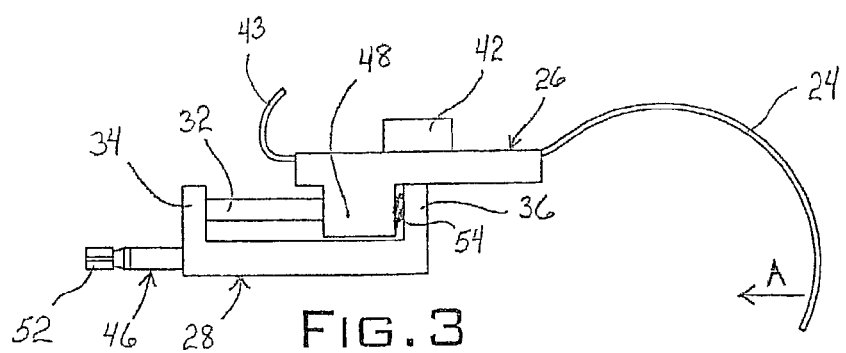
FIG. 3 is a side view of a surgical retractor assembly supporting a retracting member in a first orientation in accordance with the present invention, the retracting member, oriented as such, does not interfere with linear displacement of a retractor guide.
Figure 4:
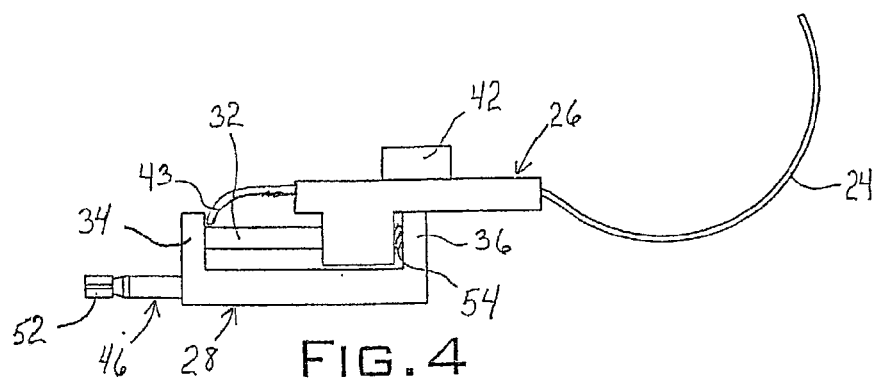
FIG. 4 is a side view of a surgical retractor assembly supporting a retracting member in a second orientation in accordance with the present invention, the retracting member, oriented as such, interferes with linear displacement of a retractor guide in this orientation.
Figure 12:
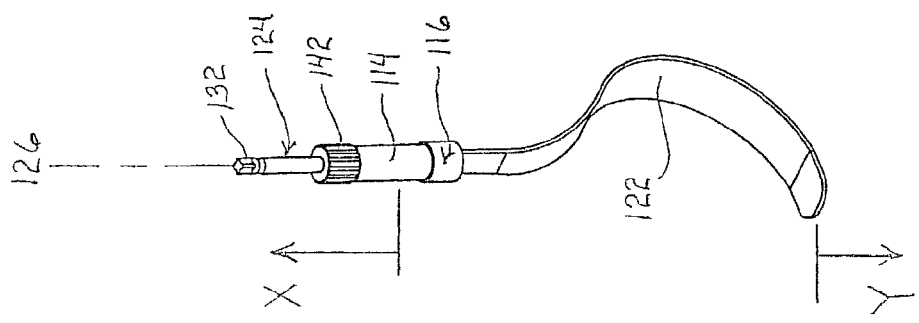
FIG. 12 is an illustrative view of a surgical retractor assembly in communication with a retracting member in accordance with the present invention.

Although the illustrative embodiments shown in FIGS. 2–4 comprise rods as the guides 32 and apertures in the communicating portion 48 of the retractor guide 26 as the compatible features of the retractor guide 26, it is understood that any compatible pair of features may be used to limit the motion of the retractor guide 26. For example, an alternative embodiment of the present invention comprises a tongue and groove arrangement (not shown) of compatible features to limit the motion of the retractor guide 26. Further, the use of a single guide at the first face 33 of the body portion 28 instead of the plurality of guides 32 illustrated in the example embodiment is also contemplated by the present invention.

The retractor guide 26 comprises a groove 38, formed in an outer face 39 of the retractor guide 26, and a locking member 42 that secures a first end of the retracting member 24 in the groove 38. The dimensions of the groove 38 are suitable to accept the first end of the retracting member 24 within the groove 38 so that the retracting member 24 is maintained in a generally linear orientation along the axis 37. As a result of this orientation of the retracting member 24, sides of the retracting member 24 are disposed adjacent and generally parallel to side walls of the groove 38. In this orientation, the retracting member 24 transmits the retracting force in a generally linear direction A (FIG. 3) along the axis 37 to a fixation site where the retracting member 24 contacts the tissue 16. Through communication between the side walls of the groove 38 and the sides of the retracting member 24, the generally linear orientation of the retracting member 24 is maintained despite the possible application of a force in a non-axial direction relative to the axis 37 during the surgical procedure.

The locking member 42 is fastened to the retractor guide 26 so that the locking member 42 contacts the retracting member 24, and thereby keeps the retracting member 24 seated in the groove 38 during the surgical procedure. Conventional fasteners 44, such as such as screws, pins, bolts, rivets, clips, or snaps, for example, or any other fastener capable of repeatedly releasing and securing the locking member 42 to the retractor guide 26 are suitable for fastening the locking member 42 to the retractor guide 26. Despite the particular fasteners 44 chosen for this application, though, the fasteners 44 must provide a force sufficient to prevent movement of the retracting member 24 in an axial direction along the axis 37 relative to the retractor guide 26.

An alternate embodiment of the present invention comprises additional locking means to provide enhanced support for the retracting member 24 in an axial direction along the axis 37. An example of such additional locking means is a protrusion (not shown) extending from a surface of the locking member 42 that contacts the retracting member 24 when installed on the surgical retractor assembly 10. The protrusion communicates with an aperture (not shown) in the retracting member 24 to prevent linear displacement of the retracting member 24 relative to the retractor guide 26.

Figure 15:
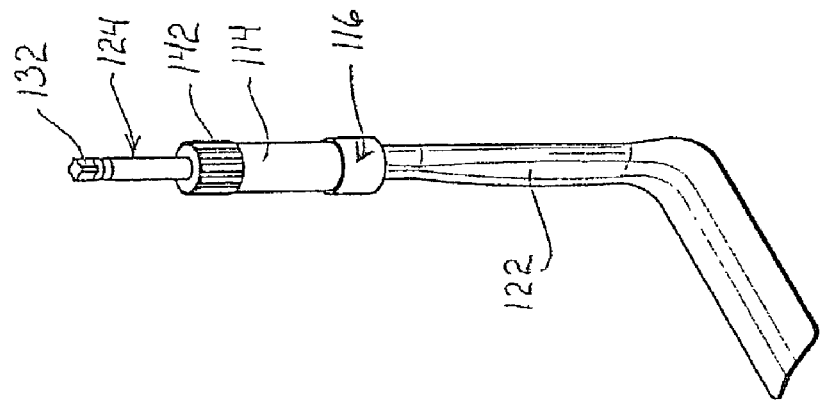
FIG. 15 is an illustrative view of a surgical retractor assembly in accordance with the present invention in communication a retracting member having the shape of a conventional Jackson Retractor.
Figure 14:
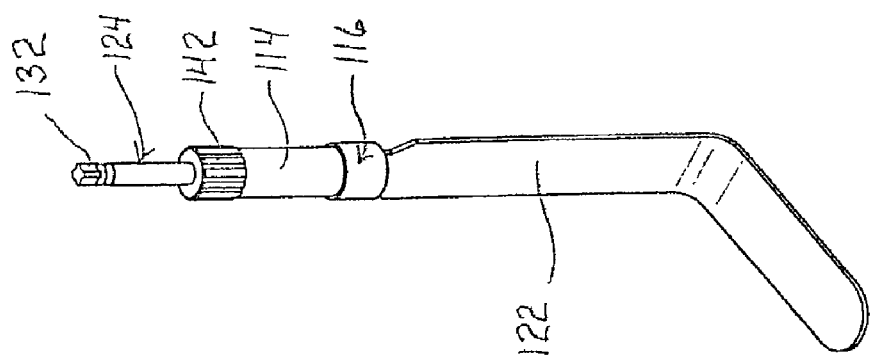
FIG. 14 is an illustrative view of a surgical retractor assembly in accordance with the present invention in communication with a retracting member having the shape of a conventional Heaney Retractor.
Figure 13:
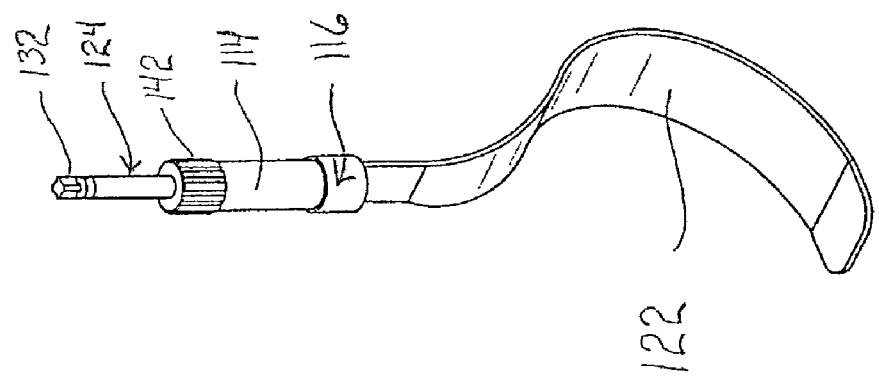
FIG. 13 is an illustrative view of a surgical retractor assembly in accordance with the present invention in communication with a retracting member having the shape of a conventional Deaver Retractor.

In general, the retracting member 24 is an arcuately shaped instrument having a stop 43 at the first end. However, the surgical retractor assembly 10 according to the present invention is capable of accepting retracting members 24 of a wide variety of shapes and sizes. For example, the embodiment of the surgical retractor assembly 10 illustrated in FIG. 2 comprises a retracting member 24 with the second end in the shape of a conventional Deaver retractor. Without attempting to produce an exhaustive list of retracting member 24 shapes and sizes, FIGS. 13–15 show, by way of example, surgical retractor assemblies 10 supporting retracting members having a second end of different shapes and sizes. FIG. 13 illustrates the surgical retractor assembly 10 according to the present invention supporting a retracting member 24 having the shape of a Deaver Retractor. FIG. 14 illustrates the surgical retractor assembly 10 according to the present invention supporting a retracting member 24 having the shape of a Heaney Retractor. And FIG. 15 illustrates the surgical retractor assembly 10 according to the present invention supporting a retracting member 24 having the shape of a Jackson Retractor.

The support structure engaging element 46 is disposed at a proximate end 47 of the body portion 28. By way of example in FIGS. 2–4, the support structure engaging element 46 is an extended member having at a first end a suitable feature 52 for communication with the support structure 14. Suitable support structures include surgical arm mechanisms well known in the art, for example, such as the surgical arm mechanism described in U.S. patent application Ser. No. 09/723,365, the disclosure of which is incorporated herein by reference.

In the example embodiments shown in FIGS. 2–4, a mechanical helical spring disposed coaxially with each of the guides 32 between the communicating portion 48 of the retractor guide 26 and the second end block 36 provides the force to displace the retracting member 24 relative to the support structure 14. Although the example embodiments above use a mechanical helical spring as a biasing structure 54, any device capable of providing the desired retracting force is within the scope of the present invention. Such biasing structures 54 include, but are not limited to, pneumatic or hydraulic actuation devices, a band of elastic material, or another appropriate known biasing structure, for example.

When the surgical retractor assembly 10 is not in use, as illustrated in FIG. 2, the retractor guide 26 is fully biased by the biasing structure 54 to an unloaded positioned at a first end of a range of linear displacement. At this position, the communication portion 48 of the retractor guide 26 is in contact with the first end block 34, preventing further linear displacement. Also with the retractor guide 26 in the unloaded position, the biasing structure 54 is fully extended as limited by the distance between the communication portion 48 of the retractor guide 26 and the second end block 36.

In use, a second end of the retracting member 24 is placed in contact with tissue 16 where a retracting force is desired. The point of contact where the second end of the retracting member 24 transmits the retracting force to the tissue 16 is the fixation site. Once in place, the position of the surgical retractor assembly 10 is adjusted to apply a retracting force at the fixation site sufficient to retract the tissue 16 without damaging it, and thereby grant the surgeon access to the subject of the surgical procedure. The force in reaction to the retracting force applied by the tissue 16 on the retracting member 24 causes the linear displacement of the retracting member 24, and accordingly, the linear displacement of the retractor guide 26, relative to the support structure engaging element 24 to an initial displacement. As the retractor guide 26 is displaced along the guides 32 from its unloaded position to its initial displacement, elastic deformation of the biasing structure 54 occurs. In the example embodiment having the spring as the biasing structure 54, the elastic deformation occurs in the form of compression of the spring between the communicating portion 48 of the retractor guide 26 and the second end block 36.

If the fixation site moves during the surgical procedure, the surgical retractor assembly 10 will accommodate such movement without releasing the retracting force on the tissue 16 at the fixation site, while minimizing the chance for injury to the patient. When the fixation site moves in a direction generally away from the surgical retractor assembly 10 as a result of movement by the patient, or an adjustment by the surgeon, for example, additional linear displacement of the retracting member 24 and the retractor guide 26 occurs to minimize damage to the tissue 16 at the fixation site from excessive stress. Thus, further elastic deformation of the spring 54 in the form of compression between the communicating portion 48 of the retractor guide 26 and the second end block 36 occurs. The amount of additional linear displacement of the retracting member 24 and the retractor guide 26 is limited by the maximum amount of compression of the spring. Maximum linear displacement of the retractor guide 26 from the unloaded position occurs when the spring is fully compressed between the communicating portion 48 of the retractor guide 26 and the second end block 36. At this point, the retracting member 24, and accordingly, the retractor guide 26 are fully extended.

In the event that the fixation site moves in a direction generally toward the surgical retractor assembly 10 due to dissection of the tissue 16, for example, the elasticity of the spring 54 provides a biasing force that reduces the degree of linear displacement 14 of the retracting member 24, and accordingly, the retractor guide 26 from the support structure engaging element 24. In other words, the distance between the communicating portion 48 of the retractor guide 26 and the second end block 36 is increased from the distance between those two features when the retractor guide 26 was at the initial displacement position. The result of this movement of the fixation site is that the retracting member 24 and the retractor guide 26 are repositioned from the initial displacement point to a second displacement point having a lesser degree of linear displacement from the support structure 14 than the initial displacement point exhibited. As the degree of linear displacement is reduced in this manner corresponding to the movement of the fixation site, the second end of the retracting member 24 is kept in contact with the tissue 16 at the fixation site, and the retracting force thereon is maintained through the elastic extension of the spring 54.

An alternate embodiment (FIG. 4) of the surgical retractor assembly 10 described above comprises a retractor guide 26 without the ability to be linearly displaced relative to a support structure engaging element 46 coupled to a body portion 28. This embodiment is generally similar to the embodiments described above, however, the retracting member has been inverted so that the stop 43 contacts the first end block 34 and thereby maintains the retracting member 24 and retractor guide 26 in the fully extended position. Thus, movement of the retractor guide 26 linearly along the axis 37 is not possible. The alternate embodiment shown in FIG. 4 is useful when the surgeon desires a rigid retractor assembly 10 without a linearly displaceable retracting member 24.

FIG. 5 is an exploded view of a surgical retractor assembly 112 according to another embodiment of the present invention. The surgical retractor assembly 112 includes a body portion 114 having a retractor guide 116 at a distal end for securing a retracting member 122 to the body portion 114, and a support structure engaging element 124 that is telescopically extendable from within the body portion 114 and biased by a biasing structure 123. A compatible feature 132 that engages the support structure 14 is disposed at an extended end of the support structure engaging element 124.

Figure 10:
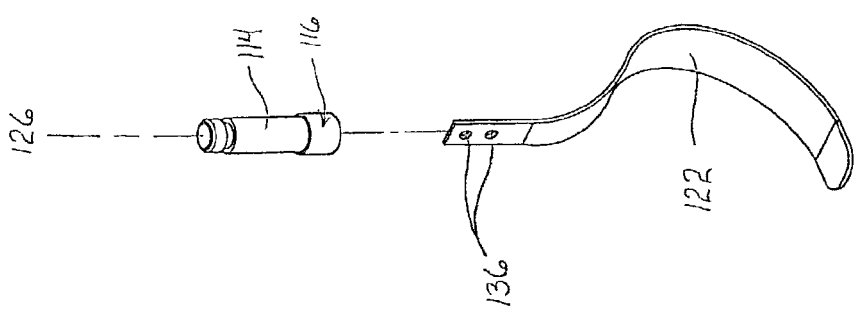
FIG. 10 is an illustrative view of the communication between a body portion, a retractor guide, and a first end of a retracting member in accordance with the present invention.

The retractor guide 116 is adapted to engage a first end of the retracting member 122 and releasably secure the first end of the retracting member 122 to the body portion 114. According to one embodiment, the first end of the retracting member 122 is disposed between side walls of a cavity 134 (FIGS. 7 and 8) formed in the retractor guide 116. An adjustable protrusion (not shown) extending from a side wall of the cavity 134 is alignable to communicate with an aperture 136 (FIG. 10) in the first end of the retracting member 122. When properly aligned, the protrusion is adjusted to provide communication with the aperture 136 by the operation of a locking mechanism 138 disposed adjacent to the retractor guide 116. The communication between the aperture 136 and the protrusion interferes with the removal of the first end of the retracting member 122 from the cavity 134.

Another embodiment of the present invention comprises an arrangement for securing the first end of the retracting member 122 to the retractor guide 116 by frictional communication between the side walls of the cavity 134 and a front and rear surface of the retracting member 122. According to such an arrangement, the aperture 136 (FIG. 10) in the first end of the retracting member 122 is not necessary. Instead, operation of the locking mechanism 138 reduces the distance between the side walls of the cavity 134, thereby providing a frictional securing force on the front and rear surface of the retracting member 122.

A cap 142 having an opening 145 (FIG. 5) through which the support structure engaging element 124 passes is removably secured at a proximate end of the body portion 114 by communication between compatible segments (not shown) on the cap and the body portion 114. An example of such compatible segments include threaded portions that can withstand the pressures exerted by the biasing structure 123 on the cap 142. As best seen in the cross sections of FIGS. 7 and 8, the inner periphery of the body portion 114 and the cap 142 define an interior cavity 143 of the surgical retractor assembly 112 through which the support structure engaging element 124 travels.

The biasing structure 123 provides a biasing force generally coaxial with the support structure engaging element 124 along the axis 126 and is disposed between the cap 142 at a first end of the biasing structure 123, and a blocking assembly 144 removably fastened to an inner end of the support structure engaging element 124 at a second end of the biasing structure 123. The blocking assembly 144 comprises at least a removable fastener 146, such as a screw, for example, having a suitably sized head 147 to prevent passage of a coil of the biasing structure 123 beyond the head 147 in an embodiment of the surgical retractor assembly 112 where the fastener 146 is the sole element of the blocking assembly 144. In another embodiment where the blocking assembly 144 further comprises a washer 148 disposed between the second end of the biasing structure 123 and the fastener 146, the head 147 of the fastener 146 must be large enough to prevent passage of the washer 148 beyond the head 147.

Figure 11:
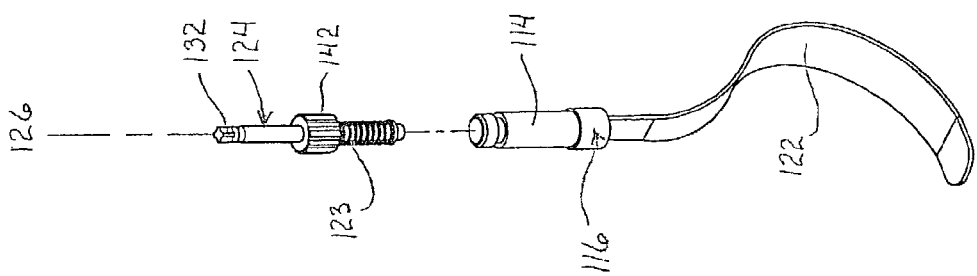
FIG. 11 is an illustrative view of the communication between a support structure engaging element and the features shown in FIG. 10.

In use, the compatible feature 132 of the support structure engaging element 124 is engaged with the support structure 14 (FIG. 1) to provide support for the surgical retractor assembly 110, and the retractor guide 116 is in communication with the first end of the retracting member 122. Initially, the surgical retractor assembly is in an unloaded state (best shown in FIG. 7) where there is no separation between the inner end of the support structure engaging element 124 and a lower portion 151 of the interior cavity 143. A surgeon, or other medical technician providing assistance during the medical procedure, positions the surgical retractor assembly 110 to locate a second end of the retracting member 122 adjacent to the fixation site. Once the second end of the retracting member 122 is properly located, the position of the surgical retractor assembly 112 is adjusted in an axial direction X (FIG. 11) generally along the axis 126 away from the fixation site so that the second end of the retracting member 122 contacts the fixation site and applies the retracting force on the tissue 16 being retracted. The adjustment of the position of the surgical retractor assembly 122 in the axial direction X along the axis 126 provokes a reactionary force exerted by the tissue 16 on the second end of the retracting member 122 in an axial direction Y (FIG. 11) generally along the axis 126. The reactionary force on the second end of the retracting member 122 causes linear displacement of the retractor guide 116 relative to the support structure engaging element 124 evidenced by the change in the distance of separation between the inner end of the support structure engaging element 124 and the lower portion 151 of the interior cavity 143 (FIGS. 7 and 8). With this degree of separation, the surgical retractor assembly is in a first retracting state (best shown in FIG. 8).

During the surgical procedure there is a distinct possibility that the fixation site will move from it's original location either towards, or away from, the support structure engaging element 124. When this occurs, the retracting member 116 moves accordingly in an axial direction along the axis 126. In the case where the fixation site moves towards the support structure engaging element 124 due to dissection of the tissue 16, for example, the biasing force provided by the biasing structure 123 causes the amount of linear displacement of the retractor guide 116 relative to the support structure engaging element 124 to decrease from the amount of linear displacement that existed when the surgical retractor assembly was in the first retracting state. Thus, the distance between the inner end of the support structure engaging element 124 and the lower portion 151 of the interior cavity 143 is less than it was when the surgical retractor assembly 112 was in the first retracting state.

In the case where the fixation site moves away from the support structure engaging element 124 due to movement of the patient, for example, the biasing force provided by the biasing structure 123 allows the amount of linear displacement of the retractor guide 116 relative to the support structure engaging element 124 to increase from the amount of linear displacement that existed when the surgical retractor assembly was in the first retracting state. Thus, the distance between the inner end of the support structure engaging element 124 and the lower portion 151 of the interior cavity 143 is greater than it was when the surgical retractor assembly 112 was in the first retracting state.

Through the above-described linear displacement of the retractor guide 126 supporting the retracting member 122, a generally constant retracting force is applied to the fixation site movement of the fixation site. Also, the linear displacement of the retractor guide 126 minimizes the risk of injury to the tissue 16 due to sudden movements of the patient during the surgical procedure.

From the above description of the invention, those skilled in the art will perceive improvements, changes and modifications. Such improvements, changes and modifications within the skill of the art are intended to be covered by the appended claims.

What is claimed is:

1. A surgical retractor assembly for providing a generally constant retracting force at a fixation site on a patient despite possible movements of the fixation site during application of the retracting force, the retractor assembly comprising:
   a tissue retracting member for retracting tissue adjacent an incision in the patient;
   a support structure engaging element for providing communication between the surgical retractor assembly and a support structure;
   a retractor guide for receiving a first end of the tissue retracting member, the retractor guide being coupled to the support structure engaging element, wherein the retractor guide is displaceable relative to the support structure engaging element; and
   a biasing structure that provides the retracting force between the retractor guide and the support structure engaging element.

2. The surgical retractor assembly according to claim 1 further comprising a body portion, wherein the retractor guide is slidably coupled to the body portion for permitting linear translation of the retractor guide relative to the body portion.

3. The surgical retractor assembly according to claim 2, wherein the support structure engaging element is an extended member comprising a feature compatible with the support structure, the feature being disposed at an extended end of the support structure engaging element, the support structure engaging element being connected to an end of the body portion in a fixed position.

4. The surgical retractor assembly according to claim 1 further comprising a body portion, wherein the retractor guide is connected to an end of the body portion at a fixed location relative to the body portion.

5. The surgical retractor assembly according to claim 4, wherein the support structure engaging element is an extended member that is telescopically adjustable at a second end of the body portion for allowing linear translation of the retractor guide relative to the support structure engaging element by telescopic communication between the support structure engaging element and the body portion.

6. The surgical retractor assembly according to claim 1, wherein the support structure is a surgical arm mechanism located adjacent to a surgical procedure.

7. The surgical retractor assembly according to claim 1, wherein the biasing structure is any one of the biasing structures selected from the group consisting of a spring, an elastic member, a hydraulic actuation device, or a pneumatic actuation device.

8. The surgical retractor assembly according to claim 1, wherein the tissue retracting member comprises an arcuately shaped instrument.

9. A surgical retractor assembly for providing a generally constant retracting force at a fixation site on a patient despite possible movements of the fixation site during application of the retracting force, the retractor assembly comprising:
   a support structure engaging element for providing communication between the surgical retractor assembly and a support structure;
   a retractor guide for receiving a first end of a retracting member, the retractor guide being coupled to the support structure engaging element, wherein the retractor guide is displaceable relative to the support structure engaging element, and wherein the retracting member is selected from the group consisting of a Deaver Retractor, a Heaney Retractor, and a Jackson Retractor; and
   a biasing structure that provides the retracting force between the retractor guide and the support structure engaging element.

10. A surgical retractor assembly for providing a generally constant retracting force at a fixation site on a patient despite possible movements of the fixation site during application of the retracting force, the retractor assembly comprising:
   means for retracting tissue adjacent an incision in the patient;
   a body portion;
   a support structure engaging element telescopically extendable from the body portion, the support structure engaging element for providing communication between the surgical retractor assembly and a support structure;

a retractor guide for receiving the means for retracting, the retractor guide being disposed at an end of the body portion; and a biasing structure that provides the retracting force between the support structure engaging element and the body portion.

11. The surgical retractor assembly according to claim 10, wherein the support structure engaging element is an extended member comprising a feature compatible with the support structure, the feature being disposed at an extended end of the support structure engaging element.

12. The surgical retractor assembly according to claim 10, wherein the biasing structure is selected from the group consisting of a spring, an elastic member, a hydraulic actuation device, and a pneumatic actuation device.

13. The surgical retractor assembly according to claim 10, wherein the support structure is a surgical arm mechanism located adjacent to a surgical procedure.

14. The surgical retractor assembly according to claim 10, wherein the means for retracting is a tissue retracting member selected from the group consisting of a Deaver Retractor, a Heaney Retractor, and a Jackson Retractor.

* * * * *